United States Patent
Enomoto et al.

[11] Patent Number: 5,878,747
[45] Date of Patent: Mar. 9, 1999

[54] CONDOM COATED WITH ACIDIC POLYSACCHARIDES

[75] Inventors: Yutaka Enomoto; Masahiko Fujii; Takao Furusho; Naoki Yamamoto, all of Tokyo, Japan

[73] Assignee: Fuji Latex Co., Ltd., Tokyo, Japan

[21] Appl. No.: 362,659

[22] Filed: Dec. 22, 1994

[30] Foreign Application Priority Data

Dec. 28, 1993 [JP] Japan .................................. 5-352000

[51] Int. Cl.⁶ ...................................................... A61F 6/04
[52] U.S. Cl. ............................................ 128/844; 128/918
[58] Field of Search .................................. 128/842, 844, 128/918; 604/347–353

[56] References Cited

U.S. PATENT DOCUMENTS

| | | | |
|---|---|---|---|
| 4,930,522 | 6/1990 | Busnel | 128/844 |
| 5,080,902 | 1/1992 | Allenmark | 128/844 |
| 5,113,874 | 5/1992 | Maronian | 128/844 |
| 5,165,953 | 11/1992 | Shienker et al. | |

FOREIGN PATENT DOCUMENTS

| | | |
|---|---|---|
| 0331821 | 2/1988 | European Pat. Off. . |
| 0292220 | 5/1988 | European Pat. Off. . |
| 0295955 | 6/1988 | European Pat. Off. . |
| 0295956 | 6/1988 | European Pat. Off. . |
| 0295961 | 6/1988 | European Pat. Off. . |
| 0319676 | 10/1988 | European Pat. Off. . |
| 0427997 | 10/1990 | European Pat. Off. . |

*Primary Examiner*—Michael A. Brown
*Attorney, Agent, or Firm*—Burgess, Ryan & Wayne

[57] ABSTRACT

A condom prophylactic against AIDS infection coated with acidic polysaccharides is provided which has an antiviral action and a method of the manufacture thereof. The acidic polysaccharides can be polysaccharides, protein-bound saccharides and glycolipids such as extracts from sea-weeds, extracts from Procaryomycota and Eucaryomycota, carrageenan and so on which have acidic groups such as sulfuric acid group in a portion of polysaccharides. A condom is coated with a solution of said acidic polysaccharides, and optionally with a lubricant. AIDS infection can be prevented without side effect by using a condom of the present invention.

15 Claims, 3 Drawing Sheets

CONDOM COATED WITH ACIDIC POLYSACCHARIDES

FIELD OF THE INVENTION

This invention relates to a condom prophylactic against AIDS infection and a method of the manufacture of such a product. In detail, it relates to a condom coated with acidic polysaccharides having an antiviral effect and a method of the manufacture thereof.

Acidic polysaccharides of, the present invention comprise polysaccharides, protein-bound polysaccharides and glycolipids which have a acidic group such as a sulfate group in a portion of the polysaccharide.

BACKGROUND OF THE INVENTION

The spread of AIDS infection has become a quite serious problem in the whole world and, especially in Asian countries, AIDS infection is wide spread.

Recently, also in Japan, the number of Japanese infected with AIDS virus (Human Immunodeficiency Virus/HIV) is increasing rapidly and the situation is the same for foreign residents in Japan. Heterosexual contact become a main infection route and is more common then homosexual contact. Thus AIDS infection is entering into a new phase and usage of a condom is definitely recommended for sexual contact.

The Notice Collection of Laws related to AIDS Countermeasures (Indispensable to AIDS countermeasures) 1992 edition, supervised by the Infectious Diseases Control Division of the Health Service Bureau of the Ministry of Welfare and Health, published by the Japanese Foundation for AIDS Prevention.

But a condom is used as formless, it sometimes happens that a condom is punctured depending on the manner to use it.

And there is a risk of spontaneous falling off of a condom from a penis during time passing as in an inserted state after sexual contact. Present inventors have been searching for material useful for the preventions of AIDS infection through a main infection route, found out that a condom coated with acidic polysaccharides having an antiviral action can be safely used for the prevention of AIDS infection.

Coating an anti-AIDS agent on a condom can double-block AIDS infection and therefore is quite useful for the prevention of AIDS infection.

SUMMARY OF THE INVENTION

The main purpose of the present invention is to provide a condom coated with acidic polysaccharides having an antiviral effect.

Another purpose of the present invention is to provide a method for the manufacture of a condom coated with acidic polysaccharides having an antiviral effect.

Acidic polysaccharides having an antiviral action used in the present invention can be used as a salt form thereof and can be a composite form combined with other components such as an antiviral agent.

Acidic polysaccharides having an antiviral action of the present invention can be obtained from sea-weeds, Procaryomycota, Eucaryomycota, Basidiomycota or seeds of dicotyldonus plants or selected from the group comprising chondroitin sulfate, carrageenan, heparin, dermatan suflate, keratan sulfate, sulfated schizophyllan, sulfated curdlan, sulfated alkyloligosaccharide, sulfated ganglioside, heparan sulfate and the salts thereof.

This antiviral action can be an anti-AIDS viral (anti-HIV) action or an antiretroviral action.

DETAILED DESCRIPTION OF THE INVENTION AND THE PREFERRED EMBODIMENTS

Figure 1:
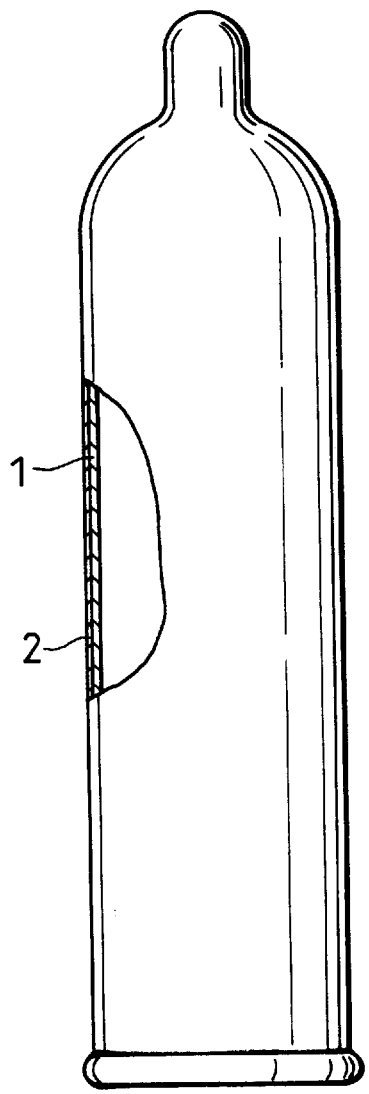
FIG. 1 is a diagramatic representation of a condom, partially cut-away, showing a coating of antiviral material on the outside.

Acidic polysaccharides having an antiviral action used in the present invention can be obtained from any type of sea-weed. For example, they can be acidic polysaccharides obtained from Phaeophyceae comprising Ectocarpales, Sphacelariales, Cutleriales, Dictyotales, Chordariales, Sporochnales, Desmaretiales, Punctariales, Dictyosiphonales, Laminariales, Fucales and so on. (Tokkai Sho 63-316731(A1))

Additionally, they can be acidic polyccharides obtained from Protoflorideophyceae or Florideophyceace comprising Porphyridiales, Goniotriales, Bangiales, Compsopogonales, Nemaliales, Gelidiales, Cryptonemiales, Gigartinales, Rhodymeniales, Ceramiales and so on. (Tokkai Sho 63-316732(A1))

In addition, they can be acidic polyusaccharides obtained from Chlorophyceae comprising Volvocales, Tetrasporales, Chlorococcales, Ulotrichales, Ulvales, Prasiolales, Shaeropleales, Cladophorales, Siphonocladales, Oedogoniales, Dasycladales, Zygnematales, Codiales and so on. (Tokkai Sho 63-316733(A1))

Acidic polysaccharides of the present invention are extracted from these sea-weeds with cold water, hot water, alkaline aqueous solution, hot alkaline aqueous solution or hydrophilic organic solvent (methanol, ethanol, isopropyl alcohol and so on) after drying and pulverization of the sea-weeds.

A low molecular weight fraction in the supernatant is removed by various method such as, salting out, dialysis, ultrafiltration, reverse osmosis, gel filtration or precipitation by addition of an organic solvent. And, if necessary, impurities can be removed by ion-exchange chromatography and the extract can be obtained by spray-drying or lyophylization. The extracts show positive or slightly positive response to α-naphthol sulfuric color reaction, indole sulfuric acid color reaction, anthrone sulfuric acid color reaction, phenol-sulfuric acid color reaction, Lowry-Folin color reaction and ninhidrin test after hydrochloric acid hydrolysis thereof.

The obtained extracts show average molecular weight of $10^3$–$10^6$ dalton.

Antiviral activity of these acidic polysaccharides is examined by a method described later in the examples and acidic polysaccharides having and antiviral action (anti-retroviral or anti-AIDS viral action) are used in the present invention.

Acidic polysaccharides used in the present invention can be obtained from Procaryomycota, such as Bacteriomycota, Myxobacteriomycota and Actinomycota belonging to Procaryomycota (Tokkai Sho 63-316726(A1)).

These Bacteriomycota can be Enterococcus faecalis (IAM-1262), Pseudomonas aeurginosa (IAM-1514), Bifidobacterium infantis (ATCC 15697), Lactobacillus casei (IAM-1118) as decsribed in the reference patent and acidic polysaccharides can be obtained from the cultured cell body thereof as described before.

In the same way acidic polysaccharides can be obtained from Eucaryomycota, such as Myxomycota, Acrasiomycota, Oomycota, Chytridiomycota, Zygomycosta, Ascomycota, Deuteromycotina and so on. (Tokkai Sho 63-316735(A1))

As examples of Eucaryomycota, cultured cell bodies of Aspergillus glaucus (IAM-3005), Saccharomyces cerevisiae (IAM-42077), Mucor spinescens (IAM-6071) and so on, can be used to obtain acidic polysaccharides in the same way as described before.

In addition, acidic polysaccharides can be obtained from Basidiomycota, especially cultured products of Basidiomycetes belonging to coliolus, for example, CM 101 cell line (FERM-P2412), CM 102 cell line (FERM-P2413), CM 103 cell line (FERM-P2414) and can be "Krestin" (Trademark by Kureha Kagaku) purified from the above cell line (Tokkai Sho 63-316734(A1), Tokkai Sho 63-366726 (A1), Tokkai Hei 1-199593(A1)) and can be obtained from dicotyldonouspiants (Seeds of *Ulex europaeus* or *Maackia amurensis*, defatted soy bean, *Canavalia glaviata*, lentil and so on.) (Tokkai Sho 63-316730(A1))

Extraction of acidic polysaccharides from these natural products can be carried out in the same way as described before.

In addition, chondroitin sulfate, carrageenan, heparin, dermatan sulfate, keratan sulfate, sulfated schizophyllan, sulfated curdlan, sulfated alkyloligosaccharides, sulfated gangliosides, heparan sulfate or the medically allowable salts therefore such as sodium salts can be used.

Acidic polysaccharides of the present invention can be used in a form of aqueous solution for coating a condom. For example, preferred wetability can be obtained by using about 10–70% of aqueous solution of acidic polysaccharides.

Acidic polysaccharides can be also used as a viscous liquid mixed into viscous material to form a coating layer. Said viscous material can be a substance able to form a viscous liquid such as creamy or greasy substance whose viscosity would be usually in the range of 5–1000 cSt.

In addition, a lubricant can be added to acidic polysaccharides. As a lubricant, monohydric alcohol, polyhydric alcohol, glycoalcohol or viscous substances can be used.

As a monohydric alcohol, isopropyl alcohol can be used, as a polyhydric alcohol, glycol or polyglycol such as glycerine, propylene glycol, diethylene alcohol can be used and as a glycoalcohol, maltitol, sorbitol and so on, can be exemplified respectively.

As a viscous substance, natural viscous substances such as alginic acid, sodium alginate, potassium alginate and gelatin or synthetic viscous substances such as carboxymethylcellulose can be exemplied.

The species and the amount of the above substance can be properly selected, considering the degree of maintaining the anti-AIDS effect of acidic polysaccharides, influence on the surface state of a condom, ease of handling and so on.

These substances can adjust the viscosity of an aqueous solution of acidic polysaccharides of the present invention and make it possibe excellent wet coating.

Further, acidic polysaccharides can be used with a lipophilic substance such as silicone oil. For example, a stable emulsion can be obtained by homogenizing an aqueous solution of acidic polysaccharides with silicone oil in a homogenizer and can be coated on the surface of a condom.

The amount of acidic polysaccharides applied on one condom is 0.001–1000 mg, preferable 0.01–100 mg. Coating on a condom is carried out on one side or to both the inner surface and the outer one.

A method of coating acidic polysaccharide on a condom, if necessary, comprises coating the whole surface or necessary portion of a condom by dropping, dipping, coating or spraying a solution containing a lubricant as described before. In this way, a condom having an antiviral effect and a lubricating effect can be obtained.

On a condom manufactured in a usual method, for example, a condom which is stripped off from a condomformer and rolled up after the forming process followed by examination process, an antiviral agent containing acidic polysaccharides is added and the condom is packaged with film to be spread with acidic polysaccharides on the whole surface thereof. As an antiviral agent, a solution of acidic polysaccharides added with a lubricant as described before can be used. In this way, a wet-type of product coated with an anti-AIDS agent in a creamy state can be obtained.

In another method, a condom can be taken from a water vessel (pinhole examination vessel) remaining on the condom former as described before, dipped in a dipping vessel (liquid vat) containing a solution of an anti-AIDS agent which comprises acidic polysaccharides having an antiviral action to be coated with acidic polysaccharides on the whole surface thereof, taken from the dipping vessel, dried, stripped off from the former and rolled up.

A solution of an anti-AIDS added to a dipping vessel can be an aqueous solution of acidic polysaccharides together with a lubricant, for example, isopropyl alcohol, as described before. In this way, a dried product coated with an anti-AIDS agent can be obtained.

In addition, on a condom, produced like this silicone oil or an aqueous solution of a lubricant can be added, followed by film packaging thereof.

The present invention is further explained by the following examples, but these examples are illustrated to exemplify the present invention and the scope of the present invention is not restricted by these examples.

EXAMPLE OF PREPARATION

At first, a concrete example of preparation of acidic polysaccharides used in the present invention is exemplified. 100 g of dried Hizikia (Phaeophyceae, Fucales, Sargassum family, Hizikia genus) was pulverized, put into a 3 l vat made of stainless steel and stirred after the addition of 2 l of water keeping the temperature of the mixture at 90°–95° C. The mixture was cooled to room temperature after being extracted for 3 hours. The extracted slurry was separated into the supernatant and the residue by centrifugation. The obtained supernatant was condensed to 400 ml under reduced pressure, lyophyllized to give about 20 g of acidic polysaccharides.

They can be used as they are. They can be further purified by ion exchange chromatography using, for example, diethylaminoethylcellulose resin and eluting adsorbed substances with salt or alkaline such as 0.5M–2M NaCl or 0.1N NaOH to give acidic polysaccharides with higher antiviral activity.

Example 1

An aqueous solution of 60% acidic polysaccharide (the viscosity thereof is about 200 cSt) was coated on a condom obtained in Example of Preparation which was formed, examined, stripped off and rolled up, followed by heat-sealing thereof. Then this solution gradually permeated and spread over the whole surface of the condom and a coated condom with wet and suitable lubricating properties was obtained. It was confirmed that the obtained condom was coated with acidic polysaccharides by the determination with phenol-sulfuric acid color reaction.

Example 2

An aqueous solution of λ-carrageenan mixed with isopropyl alcohol was put in a liquid vat as described before and a condom (while still covering a condom-former) was dipped therein after the examination for pinholes.

The condom was taken from the liquid vat, dried, stripped off from the former and rolled up. In this way a condom coated homogenously with an anti-AIDS agent was obtained.

Example 3

An aqueous solution of a lubricant consisting of propylene glycol, sodium alginate and glycerine was coated on the condom obtained in example 2, followed by heat-sealing to make the condom coated homogeneously with an antiviral agent and further with a lubricant.

An anti-AIDS action

An aqueous solution of 10 mg/ml of acidic polysaccharides (KM-101) obtained from Hizikia in the example of preparation was diluted to 5000, 1000, 200, 40, 8, 1.6 and 0.32 μg/ml at the final concentration.

$1 \times 10^{5.75}$ TCID 50/ml of HIV virus (HTLV-IIIB) solution was also prepared.

1 ml of $2 \times 10^5$/ml of MT-4 cells ($CD_4$ positive human T cell line) which is HTLV-I carrying cell line were seeded to individual wells on 24-well tissue culture plates. The above solution of acid polysaccharides was mixed with the same volume of the HIV virus solution for 5 minutes and 10 μl of the mixed solution was added to individual wells as described before. They were cultured at 37° C. in a $CO_2$ incubator.

On the 6th day of incubation, number of cell infected with HIV was counted by indirect immunofluorescence method and compared with that of the control group wherein the solution does not contain acidic polysaccharides to give an inhibition rate against infection.

| KM-101 μg/ml | Fluoresent cells(%) | Inhibition rate(%) |
|---|---|---|
| 0 | 61 | — |
| 1.6 | 43 | 30 |
| 8 | 41 | 33 |
| 40 | 6 | 92 |
| 200 | 2 | 97 |
| 1000 | 0 | 100 |

Antiviral action, anti-AIDS action 1 unit of AMV (avian myeloblastosis virus) reverse transcriptase was mixed with 50 μl of a mixture (50 mM tris hydrochloride, pH 8.4, 2 mM dithiothreitol, 100 mM KCl, 10 mM $MgCl_2$, 0.1% triton X-100, 50 μg poly (rA)-oligo (dT)/ml, 1.25 μCi [$^3$H] dTTP (57 Ci/mmol)) and with various concentration of various sulfated polysaccharides.

The reaction mixtures were incubated and stopped by the addition of 5% trichloroacetic acid. Precipitates were collected on glass fiber filters and their radio activities were determined by a liquid scintillation counter.

1 Inhibition unit is defined as an activity which inhibits 1 unit of reverse transcriptase activity to 50%.

| | Inhibition Unit/mg |
|---|---|
| λ-Carrageenan (Sigma) | 68320 |
| l-Carrageenan (Sigma) | 35810 |
| κ-Carrageenan (Sigma) | 30200 |
| Chondroitin sulfate (Seikagaku-kogyo) | 30 |
| Dermatan sulfate (Seikagaku-kogyo) | 210 |
| Heparan sulfate (Seikagaku-kogyo) | 50 |
| Karatan sulfate (Seikagaku-kogyo) | 30 |
| Heparin (Wako-junyaku) | 830 |

HIV reverse transcriptase was obtained from the culture supernatant of MOLT-4/HIV HTLV-IIIB and HIV reverse transcriptase activity was determined as described before to give nearly the same result as described before.

It has been known that such an active agent as a bis-azocompound attacking human immunodeficiency virus is coated on a sheath. (Tokkai Hei 3-501021(A1))

However, a bis-azocompound shows a strong cytocidal activity, has a severe side effect and appears to be impractical. In contrast to this, acidic polysaccharides such as sulfated polysaccharides show inhibition effects against infection which is thought to be owing to their inhibitory action against virus adsorption. Though the side effect of acidic polysaccharides such as sulfated polysaccharides is less severe than that of a bis-azocompound, it is not necessarily safe due to a side effect of inhibiting blood coagulation when they were administered systemicly (orally, parenterally).

Because the main infection route of AIDS virus relates to sexual contact, an anti-AIDS effect without any side effect during sexual contact can be obtained at high probability only by using a condom coated with polysaccharides such as sulfated polysaccharides. Furthermore, because sulfated polysaccharides do not decompose in a body, which is different from the case of oral administration thereof, an anti-AIDS effect in a practical case is surely expected as the same as that obtained from in vitro experiment, which leads to easy prediction of the effect.

FIG. 1 is an illustration, in partial cross-section, of a condom 1 coated on the outside with a layer 2 comprising a mixture of lubricant and an antiviral agent.

Figure 2:
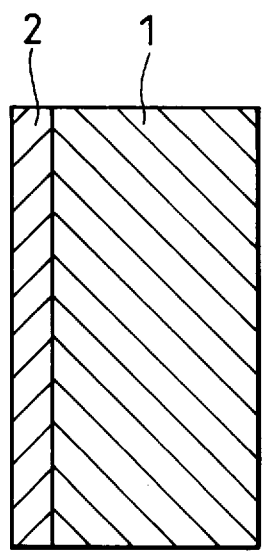
FIG. 2 is a cross-section of a portion of the coated condom of FIG. 1.

FIG. 2 is a cross-section of a portion of a condom 1 coated with a layer 2 comprising an antiviral agent. The coating is thinner than the condom 1.

Figure 3:
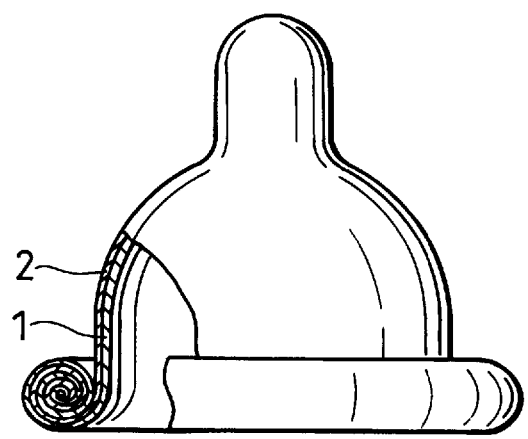
FIG. 3 is a diagramatic representation, partially cut-away, of a rolled condom of FIG. 1.

FIG. 3 is an illustration, in partial cross-section, of a rolled condom 1 coated on the outside with a layer comprising a lubricant and an antiviral agent.

Figure 4:
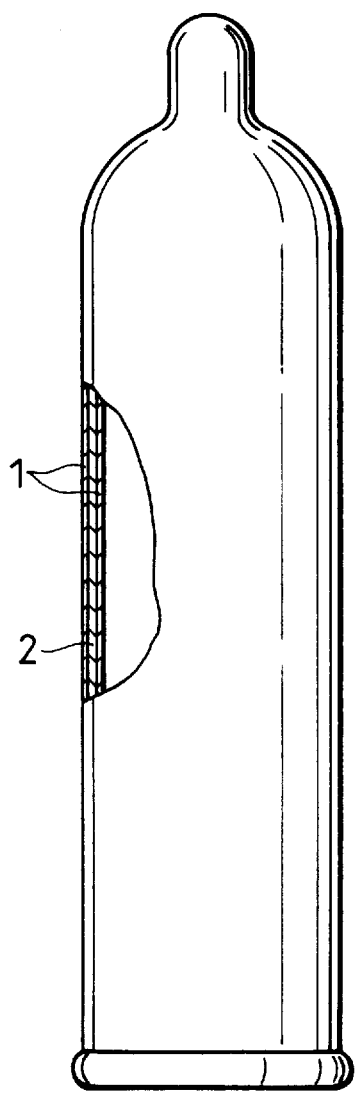
FIG. 4 is a diagramatic representation, partially cut-away, of a condom having a coating of antiviral material on the inside and the outside.

FIG. 4 is an illustration in partial cross-section of a condom 1 coated with a layer 2 comprising an antiviral agent, on the inside and the outside of the condom.

What is claimed is:

1. A condom coated with acidic polysaccharides obtained from a sea-weed and having an antiviral action to prevent AIDS infection.

2. A condom of claim 1 wherein said acidic polysaccharides having an antiviral action are obtained from a sea-weed which is selected from the group consisting of *Phaeophyceae Chlorophyceae*, Protoflorideophyceae and Florideophyceae.

3. A condom of claim 1 wherein said acidic polysaccharides having an antiviral action are obtained from Procaryomycota.

4. A condom of claim 3 wherein said acidic polysaccharides having an antiviral action are obtained from Procaryomycota which is selected from the group consisting of Bacteriomycota, Myxobacteriomycota and Actinomycota.

5. A condom of claim 1 wherein said acidic polysaccharides having an antiviral action are obtained from Eucaryomycota.

6. A condom of claim 5 wherein said acidic polysaccharides having an antiviral action are obtained from Eucaryomycota which is selected from the group consisting of Myxomycota, Acrasiomycota, Oomycota, Chytridiomycota, Zygomycota, Ascomycota and Deuterolycotina.

7. A condom of claim 1 wherein said acidic polysaccharides having an antiviral action are obtained from Basidiomycota.

8. A condom of claim 1 wherein said acidic polysaccharides having an antiviral action are obtained from seeds of dicotyldonous plants.

9. A condom of claim 1 wherein said acidic polysaccharides having an antiviral action are selected from the group consisting of chondroitin sulfuric acid, carrageenan, heparin, dermatan sulfuric acid, keratan sulfuric acid, sulfated schizophyllan, sulfated curdlan, sulfated alkyloligosaccharides, sulfated gangliosides, heparan sulfuric acid and the salts thereof.

10. A condom of claim 1 wherein said acidic polysaccharides having an antiviral action are acidic polysaccharides having an antiretroviral action.

11. A condom of claim 1 wherein said acidic polysaccharides having an antiviral action are acidic saccharides having an anti-AIDS viral action.

12. A method of manufacturing a condom prophylactic against AIDS infection comprising the steps of:

forming a condom and examining the quality thereof;

stripping off the condom from a former and rolling up the condom; and dropping a solution of acidic polysaccharides obtained from a sea-weed and having an antiviral action on the rolled condom, followed by packaging to be coated homogeneously with said acidic polysaccharides.

13. A method of manufacturing a condom prophylactic against AIDS infection comprising the steps of:

forming a condom and examining the quality thereof;

dipping the condom which covers a former into a solution of acidic polysaccharides obtained from a sea-weed and having an antiviral action;

coating the condom homogeneously with said acidic polysaccharides; and drying the condom, stripping it off from the former and rolling it up.

14. A method of manufacturing a condom prophylactic against AIDS infection comprising the steps of:

forming a condom and examining the quality thereof;

dipping the condom which covers a former into a solution of acidic polysaccharides obtained from a sea-weed and having an antiviral action;

coating the condom homogeneously with said acidic polysaccharides;

drying the condom, stripping it off from the former and rolling it up; and adding a hydrophilic or lipophilic substance to the rolled condom to add a lubricating effect thereto.

15. A condom of claim 1 wherein said acidic polysaccharides having an antiviral action comprise a carrageenan.

* * * * *

UNITED STATES PATENT AND TRADEMARK OFFICE
CERTIFICATE OF CORRECTION

PATENT NO. : 5,878,747
DATED : March 9, 1999
INVENTOR(S) : Yutaka Enomoto; Masahiko Fujii; Takao Furusho and Naoki Yamamoto It is certified that error appears in the above-indentified patent and that said Letters Patent is hereby corrected as shown below:

In Fig. 4 delete "1" and enter therefor --2--; and delete "2" and enter therefor --1--.

Signed and Sealed this

Twenty-sixth Day of October, 1999

Attest:

Q. TODD DICKINSON

Attesting Officer

Acting Commissioner of Patents and Trademarks